United States Patent [19]

Bott

[11] Patent Number: 4,490,558

[45] Date of Patent: Dec. 25, 1984

[54] PREPARATION OF THIOETHERS

[75] Inventor: Kaspar Bott, Wachenheim, Fed. Rep. of Germany

[73] Assignee: BASF Aktiengesellschaft, Ludwigshafen, Fed. Rep. of Germany

[21] Appl. No.: 510,934

[22] Filed: Jul. 5, 1983

[30] Foreign Application Priority Data

Jul. 9, 1982 [DE] Fed. Rep. of Germany ....... 3225709

[51] Int. Cl.$^3$ ............................................. C07C 149/30
[52] U.S. Cl. ...................................... 568/58; 568/38; 568/59
[58] Field of Search ........................ 568/58, 59, 60, 38

[56] References Cited

U.S. PATENT DOCUMENTS

| | | | |
|---|---|---|---|
| 3,450,771 | 6/1969 | Dombro | 568/59 |
| 3,985,718 | 10/1976 | Chabert et al. | 526/113 |
| 3,998,948 | 12/1976 | Vanlerberghe et al. | 568/45 |
| 4,267,375 | 5/1981 | Maasbol et al. | 568/58 |

OTHER PUBLICATIONS

I. Ruderman et al., J.A.C.S. 71, pp. 2264–2265, (1949).
T. Todsen et al., J.A.C.S. 72, pp. 4000–4002, (1950).
Berichte Deutsch. Chemie, vol. 1, pp. 587–591, (1935).

*Primary Examiner*—Donald G. Daus
*Assistant Examiner*—Cecilia Shen
*Attorney, Agent, or Firm*—John H. Shurtleff

[57] ABSTRACT

Thioethers are prepared by a process wherein an alkali metal mercaptide is reacted with an alcohol and carbon monoxide or with a formate, and are useful starting materials for the preparation of dyes, crop protection agents, drugs and rubber auxiliaries.

7 Claims, No Drawings

PREPARATION OF THIOETHERS

The present invention relates to a process for the preparation of thioethers by reacting an alkali metal mercaptide with an alcohol and carbon monoxide or with a formate.

Dialkyl thioethers and alkyl aryl thioethers are frequently prepared by reacting an alkali metal salt of an aliphatic or aromatic mercaptan with a conventional alkylating agent, eg. an alkyl halide, an alkyl sulfate or an alkyl sulfonate (Houben-Weyl, Methoden der Organischen Chemie, Volume IX, pages 97-116). However, these processes have the disadvantage that in many cases the stated alkylating agent has first to be prepared from the corresponding alkanol.

It has also been disclosed that a thiophenol can be reacted with ethanol over a thorium or aluminum catalyst at 350°-450° C. to give an ethyl aryl thioether. Thioethers are also prepared by reacting a phenylcarbinol with thioglycolic acid in the presence of hydrochloric acid or with p-thiocresol in the presence of formic acid, with heating. It is also possible to react a phenylcarbinol with a thiol in the presence of hydrogen chloride or boron trifluoride, or to condense tert.-butyl alcohol with thioglycolic acid in a solution containing hydrochloric acid (Houben-Weyl, loc. cit., pages 117-118). However, these reactions give satisfactory yields only in the case of an alcohol which possesses a particularly readily exchangeable hydroxyl group. With less reactive alcohols, eg. methanol or ethanol, the alkylation of the mercaptans in the above manner can be carried out only at above 350° C. A process of this type greatly restricts the choice of starting materials for the reaction, since these have to be not only readily vaporizable, but also stable at the high temperatures.

None of the above processes is simple and economical to operate and gives an end product of good purity in good yield.

I have found that thioethers of the formula $$R^1-S-R^2 \qquad \text{I}$$

where $R^1$ and $R^2$ are identical or different and are each an aliphatic, cycloaliphatic or araliphatic radical, and $R^1$ may furthermore be an aromatic radical, are advantageously obtained by reacting a mercaptan with an oxygen-containing compound, if an alkali metal mercaptide of the formula $$R^1-S-M \qquad \text{II}$$

where $R^1$ has the above meanings and M is an alkali metal atom, is reacted
(a) with an alcohol of the formula $$R^2-OH \qquad \text{III}$$

where $R^2$ has the above meanings, and carbon monoxide, or
(b) with a formate of the formula

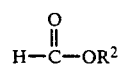
$\qquad \text{IV}$ where $R^2$ has the above meanings.

Where potassium naphth-2-ylmercaptide and methanol are used, the reaction can be represented by the following equation:

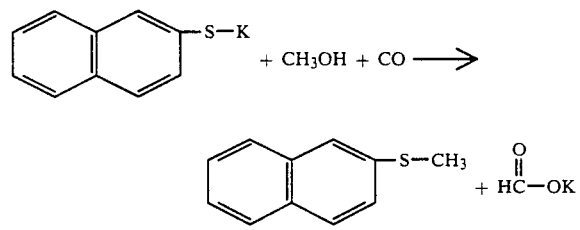

Compared with the conventional processes, the process according to the invention gives a large number of thioethers by a simpler and more economical route and in better yields. Additional catalysts or acids are not required. All these advantageous results are surprising in view of the prior art. In the reaction according to the invention, some of the alcohol III is converted to the corresponding formate IV by an addition reaction with carbon monoxide. However, a side reaction of this type surprisingly has no adverse effect on the cost efficiency of the novel thioether preparation, since the formate IV also reacts with the mercaptide II to give the thioether I.

The reaction is carried out using stoichiometric amounts of the starting materials II and III and carbon monoxide, or of starting materials II and IV, or with an excess of any of the starting materials. Advantageously, from 1 to 30, in particular from 5 to 15, moles of starting material III or from 1 to 20, in particular from 5 to 10, moles of starting material IV are employed per mole of starting material II. Preferred starting materials II, III and IV, and accordingly preferred end products I, are those of the formulae where $R^1$ and $R^2$ are identical or different and are each alkyl of 1 to 18, preferably 1 to 12, carbon atoms, cycloalkyl of 5 to 12 carbon atoms or aralkyl of 7 to 12 carbon atoms, $R^1$ may furthermore be alkylaryl of 7 to 12 carbon atoms, naphthyl or phenyl, and M is potassium or sodium. The stated radicals may be further substituted by groups which are inert under the reaction conditions, eg. alkyl, alkylthio or alkoxy, each of 1 to 4 carbon atoms.

Thus, examples of suitable starting materials II are the potassium and sodium mercaptides of methyl, ethyl, propyl, isopropyl, butyl, isobutyl, sec.-butyl, tert.-butyl, pentyl, isopentyl, hexyl, heptyl, octyl, nonyl, decyl, undecyl, dodecyl, stearyl, benzyl, cyclohexyl, cyclopentyl, phenyl, o-methylphenyl, m-methylphenyl, p-methylphenyl, naphth-1-yl and naphth-2-yl mercaptan.

Examples of suitable starting materials III are methyl, ethyl, propyl, isopropyl, butyl, isobutyl, sec.-butyl, pentyl, isopentyl, hexyl, heptyl, octyl, nonyl, decyl, undecyl, dodecyl, stearyl, benzyl, cyclohexyl and cyclopentyl alcohol, and examples of suitable starting materials IV are the esters of formic acid with these alcohols.

The reaction is advantageously carried out at from 100° to 200° C., preferably from 120° to 180° C., in particular from 140° to 160° C., and under a pressure of from 50 to 400, preferably from 100 to 320, bar, either continuously or batchwise. The above pressure is established by adding carbon monoxide to the reaction mixture at the appropriate reaction temperature, and is hence the sum of the partial pressure of the reaction mixture and the partial pressure of the CO. Where a gas mixture is used, the above reaction pressure is the sum only of the partial pressures of the reaction mixture and of the CO, and the partial pressure of the other gases has to be added on to give the total pressure, which is then, for example, advantageously from 100 to 500, preferably from 150 to 420, bar. In general, the starting materials, in particular the alcohol III or the formate IV, serve as the reaction medium, but an organic solvent, eg. an ether, such as tetrahydrofuran, dioxane or diethyl ether, or an aromatic hydrocarbon, such as benzene, toluene or a xylene, may be employed in addition, advantageously in an amount of from 100 to 2,000 percent by weight, based on starting material II. If starting material III or IV is also used as a solvent for the starting mixture, advantageously from 100 to 2,000, in particular from 200 to 600, percent by weight of III or IV, based on starting material II, is used in addition to the above amounts of III or IV which are used, or advantageously used, for the reaction.

The reaction can be carried out as follows: a mixture of starting materials II and III and carbon monoxide, or of starting materials II and IV, is kept at the reaction temperature and under the reaction pressure for from 8 to 20 hours. Advantageously, the starting materials are first combined at a low temperature, eg. from 20° to 50° C., carbon monoxide is added until the reaction pressure is established, and the mixture is heated under superatmospheric pressure for from 15 to 30 minutes until the reaction temperature is reached, and then kept at the reaction temperature and under the reaction pressure for the stated reaction time, the pressure being maintained by constantly feeding in carbon monoxide to replace the amounts consumed. If desired, the pressure may also be established and/or maintained by a mixture of carbon monoxide with an inert gas, eg. nitrogen. The end product is then isolated from the reaction mixture in a conventional manner, for example by distillation.

In a preferred embodiment, the preparation of the alkali metal mercaptide from the mercaptan, and the reaction according to the invention, are carried out by a one-pot procedure. Advantageously, the mercaptan from which starting material II is derived, the alcohol III or the formate IV, and an alkali metal alcoholate are combined at a low temperature, advantageously from 10° to 20° C., the mixture is heated and the reaction according to the invention is carried out under superatmospheric pressure, and the end product I is then isolated in the above manner. The proportion of mercaptan to starting material III or IV advantageously corresponds to the abovementioned proportion of mercaptide II to starting material III or IV. The alkali metal alcoholate used, expediently a sodium or potassium alcoholate, is advantageously that derived from the alcohol III or from the alcohol used to produce the formate IV. The alkali metal alcoholate is preferably an alkanolate of 1 to 18 carbon atoms, and is advantageously employed in the form of a 5–25 percent strength by weight solution in the alcohol III used. It is advantageous to use from 1 to 3, in particular from 1 to 1.5, moles of alkali metal alcoholate per mole of mercaptan or of starting material II to be prepared.

The thioethers obtainable by the process of the invention are useful starting materials for the preparation of dyes, crop protection agents, drugs and rubber auxiliaries. Regarding the use of these compounds, reference may be made to the above publications and to Ullmanns Encyklopädie der technischen Chemie, Volume 12, pages 292–298.

EXAMPLE 1

In a 0.3 liter stainless steel stirred autoclave, 37.9 g (0.26 mole) of n-oct-1-yl mercaptan and 20.3 g (0.29 mole) of potassium methylate were dissolved in 120 ml (3.0 moles) of methanol at 20° C., the resulting potassium octane-1-thiolate solution was heated from 20° to 150° C. in the course of 20 minutes under a carbon monoxide pressure of 300 bar, and the mixture was then kept at this temperature for 15 hours. The carbon monoxide consumed during the reaction was replaced continuously, and the pressure was kept constant at 300 bar. The mixture which emerged from the reactor was distilled under atmospheric pressure, and a methanol/methyl formate mixture was separated off and 38.2 g (92% of theory) of n-octyl methyl sulfide was obtained at 110° C./34 mbar.

EXAMPLE 2

50 g (0.31 mole) of naphth-2-yl mercaptan were introduced into a solution of 29.5 g (0.36 mole) of sodium n-propanolate and 800 ml (10.6 moles) of n-propanol, and the mixture was heated from 25° to 150° C. in the course of 60 minutes under a carbon monoxide pressure of 300 bar in a 1.2 liter stirred autoclave, and then kept at this temperature for 10 hours. The mixture which emerged from the reactor was distilled to give 58.8 g (95% of theory) of naphth-2-yl n-propyl thioether of boiling point 115°–120° C./0.6 mbar.

EXAMPLES 3 TO 11

The thioethers below were prepared by a procedure similar to that described in Example 1, except that, instead of a mercaptan and an alkali metal alcoholate, an alkali metal mercaptide was used. The composition of the starting mixture, and the results, are summarized in the Table.

TABLE

| Example | g of mercaptide II | Mercaptide $R^1$ | $R^1$—S—M M | g of alcohol III | Alcohol $R^2$—OH $R^2$ | Thioether $R^1$—S—$R^2$ Yield in % of theory |
|---|---|---|---|---|---|---|
| 3 | 93 | naphth-2-yl | K | 400 | methyl | 98 |
| 4 | 29 | naphth-2-yl | Na | 100 | ethyl | 80 |
| 5 | 62 | naphth-2-yl | K | 700 | benzyl | 95 |
| 6 | 62 | naphth-2-yl | K | 600 | n-octyl | 91 |
| 7 | 36 | n-dodecyl | K | 100 | methyl | 81 |
| 8 | 70 | n-dodecyl | Na | 650 | n-propyl | 77 |
| 9 | 20 | naphth-2-yl | Na | 120 | isopropyl | 86 |
| 10 | 28 | naphth-2-yl | Na | 120 | but-2-yl | 85 |
| 11 [a] | 30 | naphth-2-yl | K | 140 | cyclohexyl | 60 |

[a] The reaction temperature was 180° C.

EXAMPLE 12

A mixture of 30 g of potassium naphthalene-2-thiolate and 120 g of methyl formate was introduced into a 0.3 liter stirred autoclave at room temperature and heated at 150° C. for 15 hours, during which the pressure (partial pressure of CO+partial pressure of the reaction mixture) reached 210 bar. The mixture was worked up by a procedure similar to that described in Example 1 to give 23.5 g (89% of theory) of naphth-2-yl methyl thioether.

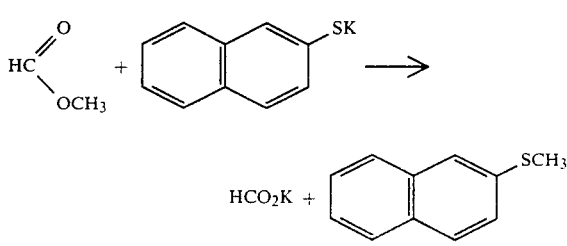

I claim:

1. A process for the preparation of a thioether of the formula $$R^1—S—R^2 \qquad \text{I}$$

where $R^1$ and $R^2$ are identical or different and are each an aliphatic, cycloaliphatic or araliphatic radical, and $R^1$ may furthermore be an aromatic radical, by reacting a mercaptan with an oxygen-containing compound, wherein an alkali metal mercaptide of the formula $$R^1—S—M \qquad \text{II}$$

where $R^1$ has the above meanings and M is an alkali metal atom, is reacted (a) with an alcohol of the formula $$R^2—OH \qquad \text{III}$$

where $R^2$ has the above meanings, and carbon monoxide, or (b) with a formate of the formula $$\overset{O}{\underset{\|}{H—C—OR^2}} \qquad \text{IV}$$

where $R^2$ has the above meanings.

2. A process as claimed in claim 1, wherein the reaction is carried out using from 1 to 30 moles of starting material III or from 1 to 20 moles of starting material IV per mole of starting material II.

3. A process as claimed in claim 1, wherein the reaction is carried out at from 100° to 200° C.

4. A process as claimed in claim 1, wherein the reaction is carried out at from 120° to 180° C.

5. A process as claimed in claim 1, wherein the reaction is carried out under a pressure of from 50 to 400 bar.

6. A process as claimed in claim 1, wherein the reaction is carried out using a gas mixture, under a total pressure of from 100 to 500 bar.

7. A process as claimed in claim 1, wherein the reaction is carried out using from 100 to 2,000 percent by weight, based on starting material II, of an additional, organic solvent.

* * * * *